(12) United States Patent
Winkler et al.

(10) Patent No.: US 9,731,092 B2
(45) Date of Patent: Aug. 15, 2017

(54) LIGHT TREATMENT APPARATUS

(76) Inventors: Engelbert Winkler, Wörgl (AT); Dirk Proeckl, Wörgl (AT)

( * ) Notice: Subject to any disclaimer, the term of this patent is extended or adjusted under 35 U.S.C. 154(b) by 1 day.

(21) Appl. No.: 13/306,884

(22) Filed: Nov. 29, 2011

(65) Prior Publication Data

US 2012/0136198 A1    May 31, 2012

Related U.S. Application Data

(63) Continuation of application No. PCT/EP2010/003381, filed on Jun. 4, 2010.

(30) Foreign Application Priority Data

Jun. 5, 2009   (DE) .................... 20 2009 007 912 U

(51) Int. Cl.
*A61M 21/00* (2006.01)
*A61N 5/06* (2006.01)

(52) U.S. Cl.
CPC .......... *A61M 21/00* (2013.01); *A61N 5/0618* (2013.01); *A61M 2021/0044* (2013.01); *A61N 2005/0652* (2013.01)

(58) Field of Classification Search
CPC .......... A61M 21/00; A61M 2021/0044; A61N 5/0618; A61N 2005/0652; A61B 5/161
USPC ......... 600/21, 27, 249; 606/2, 13; 607/1, 45, 607/54, 88, 90
See application file for complete search history.

(56) References Cited

U.S. PATENT DOCUMENTS

| 4,324,460 A * | 4/1982 | Daley ........................... 351/243 |
| 4,530,360 A * | 7/1985 | Duarte ........................... 607/51 |
| 4,940,323 A * | 7/1990 | Downing ........................ 351/203 |
| 5,309,110 A * | 5/1994 | O'Neill et al. ............... 324/674 |
| 5,403,261 A * | 4/1995 | Shimizu ............... A61M 21/00 600/27 |
| 2002/0005934 A1 * | 1/2002 | Walther ................ A61B 3/024 351/221 |

(Continued)

FOREIGN PATENT DOCUMENTS

| WO | WO 2005/118067 | 12/2005 | |
| WO | WO 2008123865 A1 * | 10/2008 | ............... H04N 9/73 |

OTHER PUBLICATIONS

TopBulb Website, "Lighting Information: Color Temperature and Color Rendering," accessed online Jun. 5, 2013, avaliable online Oct. 22, 2005 at http://www.tobpulb.com/lighting_information/info_color.asp.*

(Continued)

*Primary Examiner* — Christine H Matthews
*Assistant Examiner* — Kaylee Wilson
(74) *Attorney, Agent, or Firm* — Levine Bagade Han LLP

(57) ABSTRACT

A light treatment apparatus for simulating a psychophysical borderline experience comprises a light emitting apparatus for emitting light perceivable by the human eye as well as a control apparatus for controlling the light emission apparatus. Said light emission apparatus has at least one permanent light source as well as at least one flickering light source whose flickering light can be superimposed on the permanent light of the permanent light source in the region of a treatment area, with the control apparatus having a frequency control circuit which increases or reduces the frequency of the flickering light source from a starting frequency to a target frequency in at least one acceleration or deceleration passage.

15 Claims, 3 Drawing Sheets

(56) References Cited

U.S. PATENT DOCUMENTS

2005/0149149 A1* 7/2005 Chung et al. .................. 607/88
2006/0047324 A1 3/2006 Tass
2006/0106276 A1 5/2006 Shealy et al.
2008/0094424 A1* 4/2008 Ebe .............................. 345/690

OTHER PUBLICATIONS

Alan Li "AN-582 Resolution Enhancements of Digital Potentiometers with Multiple Devices" dated Dec. 19, 2001.*
Neetens et al. "Foveal flicker-fusion frequencies: a simple, new apparatus (4F)", Graefe's Arch Clin Exp Ophthalmol (1992) 230: 358-361.*
Mason et al. "Abnormalities of chromatic and luminance critical flicker frequency in multiple sclerosis", Invest. Ophthalmol. Vis. Sci. (Aug. 1982) 23(2): 246-252.*
International Patent Application No. PCT/EP2010/003381 filed Jun. 4, 2010 in the name of Winkler et al., International Search Report mailed Oct. 6, 2010.

* cited by examiner

LIGHT TREATMENT APPARATUS

CROSS-REFERENCE TO RELATED APPLICATIONS

This application is a continuation of PCT Application Number PCT/EP2010/003381 filed Jun. 4, 2010, which claims priority to German Patent Application Number 20 2009 007 912.0, filed Jun. 5, 2009, the content of both are incorporated herein by reference in their entireties.

BACKGROUND

The present invention relates to a light treatment apparatus for simulating a psychophysical borderline experience comprising a light emitting apparatus for emitting light perceivable by the human eye as well as a control apparatus for controlling the light emitting apparatus.

It is known that extreme psychophysical conditions can trigger physical and mental regeneration processes which result in a realignment of the total organism and make health directly experienceable. Such extreme psychophysical conditions occur, for example, during a near death experience, but also in high-performance sports or in deep meditation. Affected persons who have undergone such a borderline experience or a so-called "peak experience", frequently report an acceleration experience or tunnel experience with a particularly bright light at the end.

Such psychophysical borderline experience is accompanied by perceptible and measurable therapeutic effects on different levels. On the one hand, the therapeutic effects can range on a psychological level from a clearly perceptible elevation of mood to a strong feeling of wellbeing and even to deep psychological relaxation. On the other hand, physiologically concrete changes can be measured which become visible, for example, in an EEG or are reflected in altered blood values.

Previous light treatment devices have been used for different therapeutic purposes. It is thus known, for example, to alter the serotonin level by light irradiation of a subject in order to eliminate sleep problems, to relieve sadness and to ameliorate depressions. A corresponding light treatment device is known, for example under the trade name "Davita Light Box PhysioLight LD 220" or is also described in a similar form in DE 20 2005 010124 U1. On the other hand, for example, daylight lamps are used for irradiation of subjects to compensate for light deficiencies in winter and to relieve winter depressions.

Such devices are, however, all not suitable to induce psychophysical borderline experiences of the named kind which combine deep psychological therapeutic effects with physical therapeutic effects in the named manner.

SUMMARY OF THE INVENTION

It is therefore the underlying object of the present invention to provide an improved light treatment device for simulating psychophysical borderline experience which avoids the disadvantages of the prior art and further develops it in an advantageous manner. It is in particular intended to achieve an intense simulation of psychophysical borderline experiences with a simple device structure with only short treatment sessions.

This object is achieved in accordance with the invention by a light treatment device in accordance with claim 1. Preferred embodiments of the invention are the subject of the dependent claims.

It is therefore proposed to generate light acting on different stages of perception equally and to apply it to a subject. On the one hand, a permanent light or constant light is generated which can admittedly continuously change its light intensity or light color, but does not have any dropouts, whereas, on the other hand, a flickering light is generated which is superimposed on the named permanent light so that a subject is exposed to both light dosages simultaneously, with the flickering of the flickering light being accelerated continuously or step-wise to induce a strong acceleration effect. In accordance with the invention, the light emitting apparatus has at least one permanent light source as well as at least one flickering light source whose flickering light can be superimposed on the permanent light of the permanent light source in the region of a treatment area, with the control apparatus having a frequency control circuit which increases or reduces the frequency of the flickering light source from a starting frequency to a target frequency in at least one acceleration/deceleration cycle. Due to the combinatory effect of the two light sources, a psychophysical borderline experience can be simulated which induces intense therapeutic effects both on a psychological level and on a physical level. The frequency of the flickering light source in the acceleration/deceleration cycle can in particular be increased to a target frequency which is at least twice as high as the starting frequency. Whereas the acceleration of the flickering light frequency hereby induces a strong acceleration effect in the subject, the constant light or permanent light simulates the so-called light experience of near death or the initially named tunnel experience with a particularly bright light at the end. A strong psychophysically perceptible transcendental experience is hereby achieved which helps treat physical pain or other symptoms, but can also be used for (deep) psychological relaxation or in the wellness sector.

Provision is therefore made in this respect in a further development of the invention that the control apparatus ramps up the frequency of the dickering light source up to and at least into the range of the optical fusion limit, preferably boosts it beyond this, to induce a particularly strong acceleration effect in the subject. This acceleration effect can in this respect be achieved in a particular manner in that the frequency of the flickering light source is varied over a sufficiently large frequency range, with the magnitude of the frequency variation being adapted to the duration of the acceleration passage and/or to the time span which is required for the ramping up of the flickering light source from the named starting frequency to the target frequency.

In a further development of the invention, the target frequency is at least five times, preferably more than ten times, the starting frequency. In accordance with an advantageous embodiment of the invention, the named frequency control circuit can vary the flickering light frequency in the range from 0.1 Hz to 10,000 Hz, preferably 1 Hz to 1000 Hz, and in accordance with an advantageous embodiment from 2 Hz to 10 Hz, with optionally a variation already being able to be sufficient over a part area of this named frequency range; for example, the variation of the flickering light frequency from a starting frequency of, for example, 5 Hz to a target frequency of, for example, 50 Hz. In an advantageous further development of the invention, the frequency control circuit is, however, formed such that the flickering light frequency is variable over the whole named range.

In an advantageous further development of the invention, the frequency control circuit in this respect has adjustment means for the variable setting of the starting frequency and/or for the variable setting of the target frequency, with the starting frequency advantageously being able to be selected as desired in the named variation range, preferably at least in its lower half, and with the target frequency likewise being able to be selected over the total named variation range, preferably at least in its upper half.

The named frequency control circuit advantageously has, in a further development of the invention, a frequency accelerator circuit which increases the flickering light frequency continuously or in multiple stages, in particular in at least more than three stages, preferably more than ten stages, from the named starting frequency to the target frequency. This allows the flickering light frequency to be conducted slowly from the starting frequency to the target frequency, i.e. the frequency acceleration is not carried out abruptly, but rather step by step or continuously, to carry the subject along into the acceleration process.

Alternatively or additionally, an input circuit can also be provided, preferably in the form of a hold-to-run control device, which is activated manually to allow a manual triggering of the flickering light and/or control of the flickering light frequency or the on/off phases of the flickering light.

The duration of an acceleration passage can advantageously be set variable, with the time span which is required to increase the flickering light frequency from its starting frequency to the target frequency advantageously being selected in the range from 1 min to 1 hr. In order, on the one hand, to carry the subject safely along in the acceleration process, but, on the other hand, to achieve a short, efficient treatment time, the adjustable timer for the acceleration passage provides a time span of preferably more than 5 min, optionally also more than 10 min, but usually less than 30 min.

To achieve an intense therapeutic effect, it can be advantageous if the control apparatus performs such acceleration passages after one another, optionally interrupted by rest periods. In accordance with an advantageous further development of the invention, the control device can provide two to three acceleration passages of, advantageously, a total of 20 to 40 min duration.

The light intensity of the permanent light source and also the light intensity of the flickering light source can generally be selected as different. Provision is made in this respect in a further development of the invention that the luminance of the permanent light can be varied in the region of the treatment area, for example by varying the luminous flux emitted by the permanent light source. A dimmer can be associated with the permanent light source for this purpose.

In a further development of the invention, adjustment means are associated with the permanent light source for the variable setting of the luminance of the permanent light in the region of the treatment area which are controlled by the control apparatus in dependence on the operating state of the flickering light source. The control apparatus can in particular have a luminance control circuit which controls the named luminance of the permanent light in dependence on the flickering light frequency such that the luminance of the permanent light is lower at the start of the acceleration passage of the flickering light than at the end of the named acceleration passage. The luminance of the permanent light in particular reaches its maximum only when the frequency of the flickering light source is moved into the range of optical fusion in which the light pulses of the flickering light fuse in the perception of the subject to form a permanent or constant light.

Alternatively or additionally, the luminance of the permanent light can also be controlled independently of the operating state of the flickering light source and/or, conversely, the operating state of the flickering light source can be controlled independently of the luminance of the permanent light. A manual actuator or regulator can be provided for this purpose, for example. Equally, the maximum of the permanent light can optionally also already be reached before the reaching of the fusion border of the flickering light.

The control apparatus can in this respect generally provide a stepless, constant ramping up or also a stepped ramping up of the luminance of the permanent light. An increase of the luminance of the permanent light is advantageously provided which differs from a constant increase and which increases progressively toward the end of the acceleration cycle to simulate the named light at the end of the tunnel more intensely.

The luminance and the light intensity respectively of the permanent light and/or of the flickering light can be different. For example, a respective luminous flux of 500-1500, preferably 700-900 lumen, and/or an illuminance of 2000-3000 lx and/or a light intensity of 100-300 cd, preferably 200-250 cd, can be provided.

In an advantageous further development of the invention, the permanent light source or the permanent light emitted by it have a different color temperature than the flickering light source or the flickering light emitted thereby. It is in particular of advantage in this respect if the at least one permanent light source emits warmer light than the at least one flickering light source. The combinatory' synergetic effect of the differently working light sources is hereby increased. The light pulses of the flickering light are perceived more intensely, harder due to colder light, whereas the warmer permanent light better simulates the actual light experience of near death or of the experience borderline. The color temperatures specifically to be chosen can in this respect be varied in dependence on the treatment type and on the subject, with the permanent light source preferably emitting warm light and the flickering light source cold light. An advantageous embodiment of the invention can in this respect comprise the permanent light of the permanent light source having a color temperature in the range from 1500 to 3500 K, preferably 2000 to 3000 K, and the flickering light source or the flickering light emitted thereby having a color temperature from approximately 4000 to 10,000 K, preferably 5000 to 8000 K. A halogen spot can, for example, be used as the permanent light source and LEDs as the flickering light source.

BRIEF DESCRIPTION OF THE DRAWINGS

The invention will be explained in more detail in the following with respect to a preferred embodiment and to associated drawings. There are shown in the drawings.

DETAILED DESCRIPTION

Figure 1:
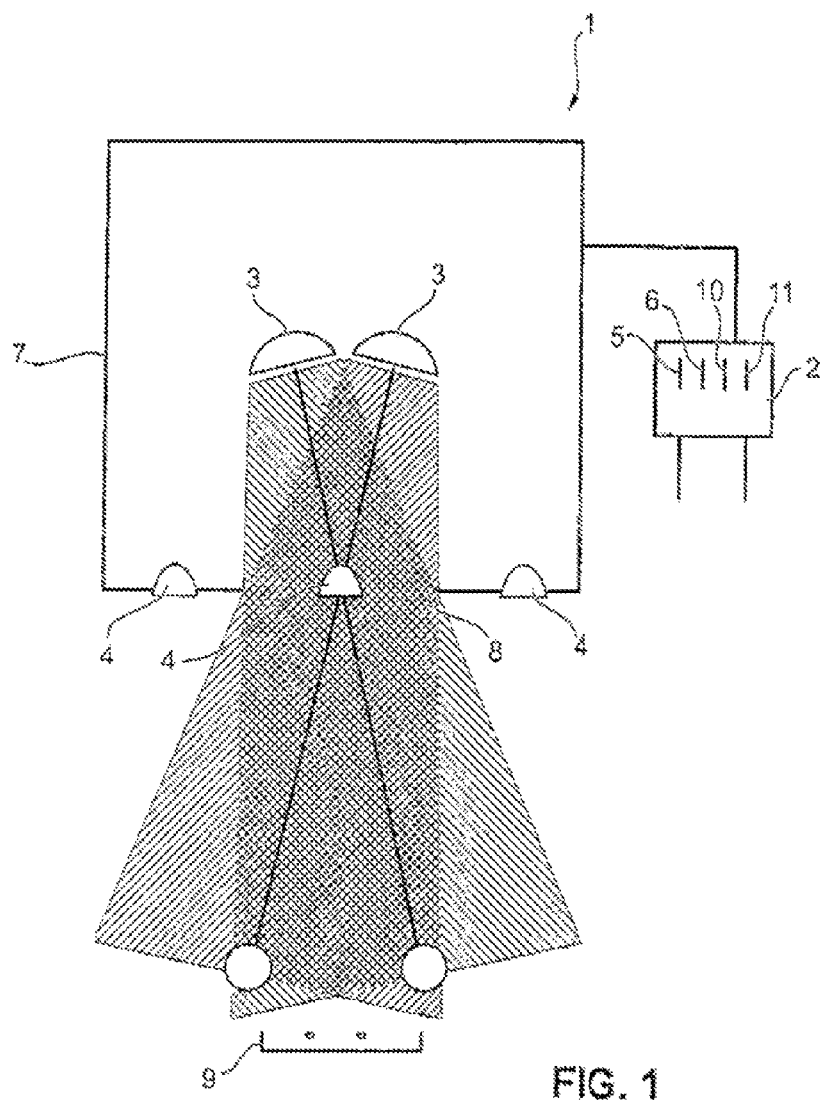
FIG. 1 a schematic representation of a light treatment device in the construction form of a lamp-like standalone device in accordance with a possible advantageous embodiment of the invention, in accordance with which a plurality of permanent light sources in the form of halogen sports are combined with a plurality of flickering light sources in the form of LEDs to superimpose flickering light with permanent light in a treatment area.

The embodiment of the invention shown by way of example in Fig. 1 shows a light emitting apparatus 1 which is designed as a lamp-like standalone device. It is, however, understood that the different light sources do not have to be combined in a device forming the unit or even installed in a standalone housing even if this represents an advantageous embodiment but can also be designed as a room installation, which allows a spatially flexible positioning of the individual light sources, or also as a mobile device wearable like eyeglasses.

Figure 2:
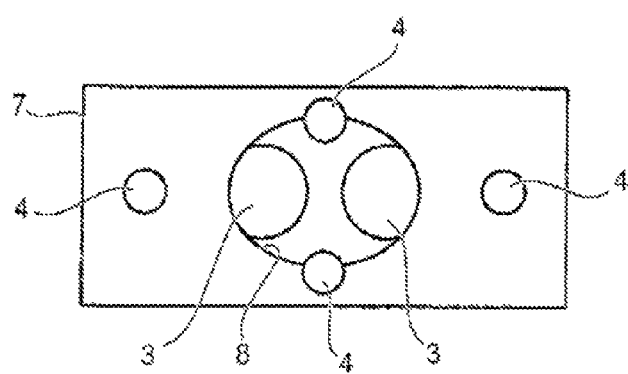
FIG. 2 a front view of the light treatment device of FIG. 1.

In the embodiment drawn in FIGS. 1 and 2, the light emitting apparatus 1 in this respect comprises a light source carrier 7 which can form a housing and/or can be designed in the manner of a diaphragm. In the embodiment drawn, two permanent light sources 3 in the form of halogen spots are in this respect arranged behind a diaphragm aperture 8 and their light cone is directed through the diaphragm opening 8 and/or through an optical device, not drawn separately, such as a reflector and/or a lens onto a treatment area 9 so that the light cone emitted by the permanent light sources 3 is incident onto the eyes of the subject.

The named light source carrier 7 furthermore carries a plurality of flickering light sources 4, with four LEDs being provided as flickering light sources 4 in the drawn embodiment which are arranged symmetrically with respect to the arrangement of the permanent light sources 3 or of the diaphragm opening 8. In the drawn embodiment, the flickering light sources 4 are in this respect arranged outwardly around the light cone of the permanent light sources 3 emerging from the light source carrier 7 so that the permanent light source 3 projects so-to-say from the center of the flickering light sources.

The light cones of the flickering light sources are also directed to the eye position of the subject located in the treatment area 9.

Figure 3:
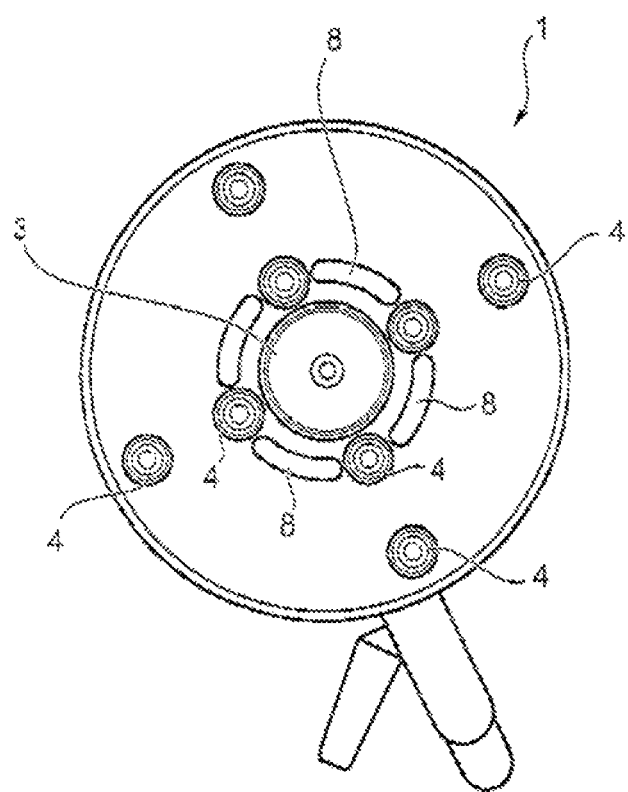
FIG. 3 a front view of the light treatment device in accordance with a further embodiment.

As FIG. 3 shows, the light emitting apparatus 1 can also have only one permanent light source 3 which is centrally positioned in accordance with FIG. 3 and is surrounded by a total of eight flickering light sources 4 which are arranged symmetrically distributed over two rings.

The light sources 3 and 4 are controlled by a control apparatus 2 which can generally have different designs. In the drawn embodiment, it comprises a permanent light control circuit 10 as well as a flickering light control circuit 11 which control the operation of the permanent light sources 3 or of the flickering light sources 4 with respect to emitted light intensity and pulsing.

The flickering light control module 11 in this respect comprises a frequency control module 5 by means of which the frequency of the flickering light is varied. The named frequency control module 5 can advantageously include a pulse width control module in order also to vary the pulse width of the light pulses of the flickering light so that not only the frequency of the light pulses can be varied, but also the ratio of the duration of a light pulse to a non-radiation time following or preceding it.

The named permanent light control circuit 11 can in particular include a luminance control circuit to be able to vary the luminance of the permanent light in the region of the treatment area 9, which can be effected, for example, in a simple manner by a luminous intensity regulator.

Figure 4:
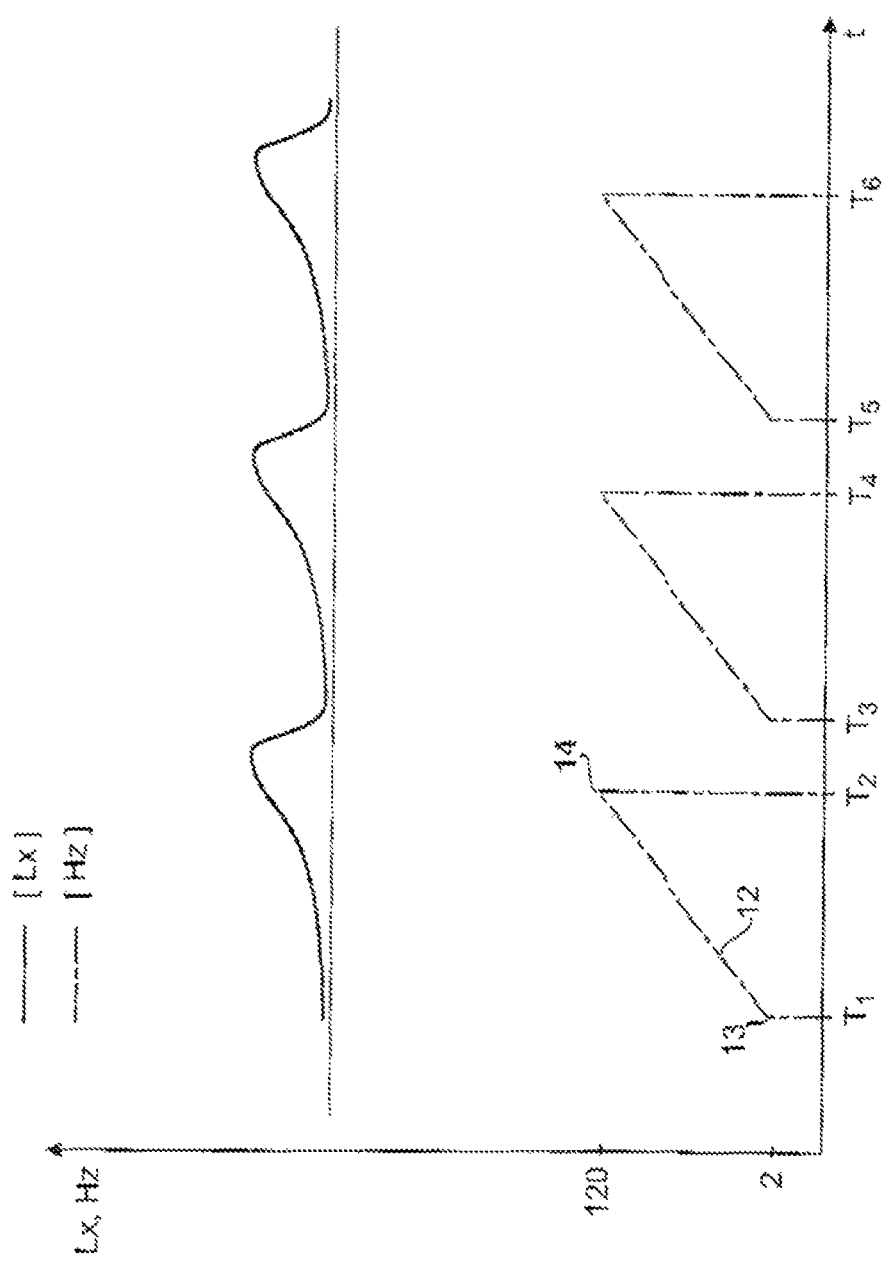
FIG. 4 a flowchart to illustrate the variation of the flickering light frequency during a plurality of sequential acceleration passages and the change, matched thereto, of the luminosity of the permanent light source in accordance with a possible advantageous embodiment of the invention, with the solid line indicating the luminosity of the permanent light source in lx and the chain-dotted line indicating the frequency of the flickering light source in Hz.

FIG. 4 shows by way of example a possible operating cycle of the apparatus from FIGS. 1 and 2. As FIG. 4 shows, the flickering light frequency 12 shown by chain dotting is continuously increased in a plurality of sequential acceleration cycles $T_1$ to $T_2$, $T_3$ to $T_4$ and $T_5$ to $T_6$, from a starting frequency 13 to a target frequency 14, with the named target frequency 14 advantageously being just above the optical fusion limit. The time spans $T_1$ to $T_2$, $T_3$ to $T_4$ and $T_5$ to $T_6$, can advantageously be in the range from some minutes, for example between 5 and 10 minutes. In the drawn embodiment, the flickering light frequency 12 is in this respect increased with a constant gradient from initially 2 Hz to 120 Hz. Relaxation breaks are provided between the individual acceleration cycles whose lengths can be differently dimensioned.

The luminous intensity of the permanent light sources 3 is also varied in manner adapted in time to the variation of the flickering light frequency; In the exemplary embodiment drawn in FIG. 4, the light intensity of the permanent light sources 3 is in this respect first increased only increasing slowly during an acceleration cycle $T_1$ to $T_2$ and is only increased more toward the end of the acceleration cycle so that the maximum luminous intensity of the permanent light sources 3 is only reached at the end or shortly after the reaching of the target frequency 14 to simulate the initially mentioned light at the end of the tunnel. As FIG. 4 shows, a plurality of acceleration cycles can be worked through with a corresponding adaptation of the permanent light sources.

We claim:

1. A light treatment apparatus comprising:
a light emitting apparatus for emitting light which is perceivable via the human eye, wherein the light emitting apparatus comprises a permanent light source configured to emit a permanent light, and a flickering light source configured to emit a flickering light superimposed on the permanent light, wherein the permanent light source has a warmer color temperature than the flickering light source; and
a light emitting control apparatus comprising a frequency control circuit configured to automatically increase a frequency of the flickering light source from a starting frequency to a target frequency above an optical fusion limit of a subject in an acceleration cycle, wherein the frequency is configured to vary over a fixed time span and cross the optical fusion limit, wherein the target frequency is above the optical fusion limit and at least twice as high as the starting frequency; and an adjustment element for variable setting of a luminance of the permanent light source in a treatment area, wherein the adjustment element is configured to be controlled by the light emitting control apparatus in dependence on the frequency of the flickering light source, wherein the adjustment element is configured to control the luminance of the permanent light source such that the luminance is lower at the starting frequency of the flickering light source and only reaches a maximum luminance on reaching the target frequency of the flickering light source.

2. The apparatus of claim 1, wherein the target frequency is at least five times the starting frequency.

3. The apparatus of claim 2, wherein the target frequency is in the range of the optical fusion limit.

4. The apparatus of claim 1, wherein the target frequency is more than ten times the starting frequency.

5. The apparatus of claim 1, wherein the frequency control circuit has a variable frequency range from 0 Hz to 1.6 kHz, and the flickering light frequency varies over a range of at least 20 Hz.

6. The apparatus of claim 5, wherein the frequency control circuit has a variable frequency range from 2 Hz to 160 Hz.

7. The apparatus of claim 5, wherein an adjustment element for variable setting of the starting frequency and for variable setting of the target frequency is associated with the frequency control circuit.

8. The apparatus of claim 1, wherein the frequency control circuit comprises a frequency accelerator which increases the flickering light frequency continuously or in multiple stages from the starting frequency to the target frequency.

9. The apparatus of claim 8, wherein the frequency accelerator is configured to increase the flickering light frequency in more than three stages from the starting frequency to the target frequency.

10. The apparatus of claim 1, wherein the light emitting control apparatus comprises a timer which provides an acceleration passage over a time span of at least 1 minute.

11. The apparatus of claim 10, wherein the timer provides the acceleration passage over a time span of more than 5 minutes.

12. The apparatus of claim 1, wherein the permanent light source has a color temperature in a range from 1500 K to 3500 K and wherein the flickering light source has a color temperature from 4000 K to 10,000 K.

13. The apparatus of claim 1, wherein the permanent light source has a color temperature in a range from 2000 K to 3000 K and wherein the flickering light source has a color temperature from 5000 K to 8000 K.

14. A method for light treatment comprising:
  emitting light from a light emitting apparatus, wherein the emitted light is perceivable via the human eye, wherein the light emitting apparatus comprises a permanent light source configured to emit a permanent light, and a flickering light source configured to emit a flickering light superimposed on the permanent light, wherein the permanent light source has a warmer color temperature than the flickering light source; and
  controlling the light emitting apparatus by a control apparatus, wherein the control apparatus comprises a frequency control circuit which automatically increases a frequency of the flickering light source from a starting frequency to a target frequency in an acceleration cycle; wherein the target frequency is above an optical fusion limit and at least five times the starting frequency; and an adjustment element for variable setting of a luminance of the permanent light source in a treatment area, wherein the adjustment element is configured to be controlled by the control apparatus in dependence on the frequency of the flickering light source, wherein the adjustment element is configured to control the luminance of the permanent light source such that the luminance is lower at the starting frequency of the flickering light source and only reaches a maximum luminance on reaching the target frequency of the flickering light source.

15. A light treatment apparatus comprising:
a light emitting apparatus for emitting light which is perceivable via the human eye, wherein the light emitting apparatus comprises a permanent light source configured to emit a permanent light, and a flickering light source configured to emit a flickering light superimposed on the permanent light, wherein the permanent light source has a warmer color temperature than the flickering light source; and
a control apparatus comprising a frequency control circuit configured to automatically increase a frequency of the flickering light source from a starting frequency to a target frequency in an acceleration cycle, wherein the target frequency is above an optical fusion limit and at least five times the starting frequency, wherein the frequency is configured to vary up to at least 50 Hz; and an adjustment element for variable setting of a luminance of the permanent light source in a treatment area, wherein the adjustment element is configured to be controlled by the control apparatus in dependence on the frequency of the flickering light source, wherein the adjustment element is configured to control the luminance of the permanent light source such that the luminance is lower at the starting frequency for the flickering light source and only reaches a maximum luminance on reaching the target frequency of the flickering light source.

* * * * *